United States Patent

Buglino et al.

Patent Number: 5,204,062
Date of Patent: Apr. 20, 1993

[54] BOWIE-DICK TEST DEVICE

[75] Inventors: Steven T. Buglino, Apex; Pareshbhai J. Patel, Cary; Bahram B. Rahimzadeh, Durham, all of N.C.

[73] Assignee: Surgicot Incorporated, Research Triangle Park, N.C.

[21] Appl. No.: 402,379

[22] Filed: Sep. 5, 1989

[51] Int. Cl.$^5$ ............................................. G01N 31/22
[52] U.S. Cl. ........................................ 422/56; 422/57; 422/58; 436/1; 436/2
[58] Field of Search ................ 422/55, 56, 57; 436/1, 436/2

[56] References Cited

U.S. PATENT DOCUMENTS

| 3,811,840 | 5/1974 | Bauer et al. |
| 3,862,824 | 1/1975 | Chapman |
| 3,981,683 | 9/1976 | Larsson et al. |
| 3,996,802 | 12/1976 | Smith |
| 4,121,714 | 10/1978 | Daly et al. |
| 4,382,063 | 5/1983 | Amito et al. |
| 4,410,493 | 10/1983 | Joslyn |
| 4,448,548 | 5/1984 | Folely |
| 4,486,387 | 12/1984 | Augurt |
| 4,514,361 | 4/1985 | Hirsch |
| 4,579,715 | 4/1986 | Bruso |
| 4,594,223 | 6/1986 | Dyke et al. |
| 4,596,696 | 6/1986 | Scoville, Jr. |
| 4,636,472 | 1/1987 | Bruso |
| 4,692,307 | 9/1987 | Bruso |
| 4,699,765 | 10/1987 | Hambleton |
| 4,757,014 | 7/1988 | Hendrickson et al. |
| 4,758,229 | 7/1988 | Doerschner |
| 4,758,230 | 7/1988 | Rycroft |
| 4,758,231 | 7/1988 | Haber et al. |
| 4,758,509 | 7/1988 | Ottley |
| 4,772,560 | 9/1988 | Attar |

FOREIGN PATENT DOCUMENTS

WO88/04939  7/1988  PCT Int'l Appl.

Primary Examiner—Jill A. Johnston

[57] ABSTRACT

A permanent record test device tests the efficiency of a steam sterilizer apparatus to create a vacuum satisfying the Bowie-Dick test procedure. A sheet of selectively porous material such as one hundred pound blotter paper having a steam sensitive indicator ink printed thereon is laminated between layers of steam and air impermeable polymeric material to substantially occlude the sheet from ambient atmosphere, except for a small metering region. The small metering region may include a hole punched through the laminated sheet. Two parallel and spaced apart strips can be used with a metering hole punched at one end of each of the strips or, alternatively, a metering hole is punched at one end of any one of the strips and the strips can be connected with a fluid passageway at the opposite end of the strips. Strips other then straight strips can be used, e.g., an L-shaped strip can be used with a V-shaped strip.

7 Claims, 2 Drawing Sheets

BOWIE-DICK TEST DEVICE

BACKGROUND OF THE INVENTION

This invention relates to a method and apparatus for determining the efficiency of a vacuum in a steam sterilizing apparatus. More particularly, the invention is directed to a test device that meets the Bowie-Dick test procedure.

Steam sterilization is a common method of sterilizing items in health care centers and is enhanced when the items are subjected to a vacuum prior to exposure to steam. Since the presence of air can compromise steam penetration into the items being sterilized, a test had to be devised to indicate if any air was present after being subjected to a vacuum.

Such a test was developed by J. H. Bowie and J. Dick and published in an article appearing in "The Lancet", Mar. 16, 1963, pages 586-587. It utilizes a sheet of paper to which a steam sensitive tape is applied in the fashion of a St. Andrew's cross. The sheet is placed in the center of a stack of towels and the combination is then placed in the front bottom of an empty sterilizer chamber and then subjected to a vacuum steam cycle. If for any reason residual air is present in the pack or the chamber, its presence is detected by this construction. It is believed that when steam is introduced into the chamber, any residual air is pushed to the center of the pack or drawn into the pack by pressure differentials. This is shown by the center of the cross pattern showing no reaction to steam presence. If no air were present, the cross pattern would be uniformly changed in color.

This construction was used (with minor changes) until 1982, when Augert (U.S. Pat. No. 4,486,387) taught that various porous papers can be reliably substituted for towels, and then stacked in such a way as to form a pack equivalent to the original Bowie-Dick test pack. In 1983, Bruso (U.S. Pat. No. 4,579,715) taught that by partially occluding the outer surface of this stack of sheets, only one porosity value for the paper need be used and the size of the paper could be reduced. Both patents rely on the porous nature of the specific papers.

Bruso teaches that non-porous layers can be placed on a pack of porous layers to reduce the surface area of exposed porous material to establish a more challenging test for the evacuation of air and introduction of steam. This also results in a smaller test pack, but Bruso's pack still requires porous pads such as a stack of blotter papers disposed on either side of an indicator sheet.

An ideal Bowie-Dick test device should not be larger than necessary and should be easily manufactured, reliable and consistent. It should not generate any waste material and it should become a permanent test record. An object of the present invention is to provide such an improved Bowie-Dick test device.

SUMMARY OF THE INVENTION

The present invention provides for a method of constructing a permanent record test device for testing the efficiency of a steam sterilizer apparatus to create a vacuum satisfying the Bowie-Dick test procedure. The method comprises laminating a sheet of selectively porous material having a steam sensitive indicator ink printed thereon between layers of steam and air impermeable polymeric material to substantially totally occlude the sheet from ambient atmosphere except for a small metering region whereby a meaningful challenge to the evacuation of air is created. The small metering region is preferably formed after laminating the sheet and comprises forming at least one hole through the laminated sheet. Preferably the sheet of selectively porous material comprises 100 pound blotter paper stock. Alternatively, the sheet could comprise at least two parallel and spaced apart strips, each being substantially, totally occluded except for a small metering region such as a hole punched through each laminated strip. When laminating the two parallel spaced apart strips, the method may further comprise connecting the strips within the laminated layers with a fluid passage way. The invention further provides for a permanent record test device for testing the efficiency of a steam sterilizer apparatus to create a vacuum satisfying the Bowie-Dick test procedure. The permanent record includes a sheet with a steam sensitive indicator ink printed thereon comprising a selectively porous material such as 100 pound blotter paper stock. The permanent record further comprises at least two layers of steam and air impermeable polymeric material laminated on either side around the edges of the sheet to substantially occlude the sheet from ambient atmosphere, except for a small metering region. The small metering region may include a hole formed or punched through the laminated sheet. Alternatively, the sheet could comprise two parallel and spaced apart strips, each being substantially totally occluded except for a small metering region such as a punched hole. In an alternate embodiment, the two strips could be connected by a fluid passage way between the laminated layers. In such a device the small metering region comprises a hole formed through only one of the strips near to but spaced apart from a first end of the strip and the fluid passage way is formed near or to the opposite end.

DETAILED DESCRIPTION OF THE DRAWINGS

Figure 1:
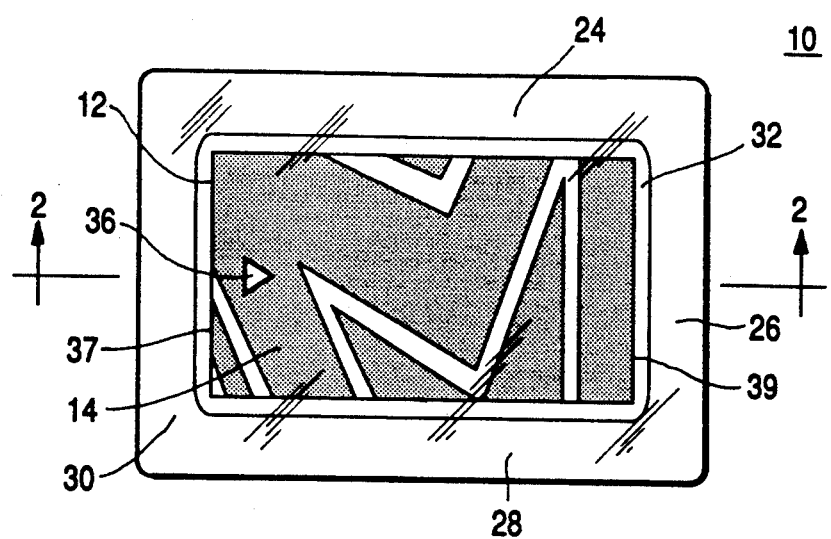
FIG. 1 is a top planar view of the Bowie-Dick test device of the present invention.

Referring initially to FIG. 1, a Bowie-Dick test device according to the present invention is designated generally 10. It comprises a substrate 12 imprinted with any pattern of indicator ink 14 which will indicate or detect the presence of a steam sterilization medium. Any indicator ink 14 which changes color in the presence of steam is acceptable. The substrate is preferably a sheet of a selectively porous material suitable for the purpose, for example, a material formed as an entanglement of fibrous material and suitable for printing with indicator ink. One suitable material is one hundred pound blotter paper but other similar substrates will be equivalent.

In the device of the present invention the sheet 12 is rectangular and is laminated with clear plastic film layers 20 and 22 on the sheet's top and bottom surfaces and around all four edges in the regions 24, 26, 28 and 30. Suitable polymeric materials should be impermeable and have the ability to withstand the stresses of steam sterilization, e.g., a polyester/polyethylene copolymer film having a total thickness of 10 mils is acceptable. During the lamination process a small region 32 exists adjacent to and around the periphery of the layer 12 wherein the plastic layers 20 and 22 are not laminated together because of the thickness of the sheet 12. The lamination is intended to totally occlude as much as possible of the sheet 12 from ambient atmosphere. Afterwards, a small metering hole 36 is punched through the layers 20 and 22 and the sheet 12. This exposes the sheet 12 to ambient atmosphere around the periphery of the hole. By varying the size, shape and location of the hole the amount of exposure of the selectively porous sheet 12 to ambient atmosphere can be greatly controlled. Also, the location of the metering hole will most likely be centered along the lengthwise centerline of the sheet but closer to end 37 than opposite end 39.

The device 10 is placed in the chamber to be tested. A vacuum is drawn and then a steam cycle is completed. When the vacuum is drawn, air trapped in the selectively porous sheet 12 near the metering hole 36 leaves the device first. Depending on the strength of the vacuum, air from the end remote from the hole 36 near edge 39 will be the last air to be evacuated. This air must leave through hole 36 since the sheet 12 is otherwise totally occluded. If any air remains when steam is introduced into the chamber, the remaining air will recede or be forced to the end of the sheet 12 farthest from hole 36. This remaining air will prevent steam from contacting the indicator ink 14 to turn it to a darker color. Depending on the amount of air remaining, the length of the sheet 12 which turns color will be longer or shorter. The more efficient the vacuum the more the length of the layer is darkened.

While a hole punched through the device 10 is shown and described herein, the sheet 12 may be exposed to ambient atmosphere along a portion of its perimeter by eliminating the lamination along a portion of an edge or edges. The significance of this invention is that this single laminated sheet 12 provides a test device which meets the Bowie-Dick test procedure where heretofore it was thought necessary to provide an indicator sheet in the center of a stack of towels or porous papers. Lamination of a selectively porous sheet with a controlled size metering port provides a suitable Bowie-Dick test device.

Figure 3:
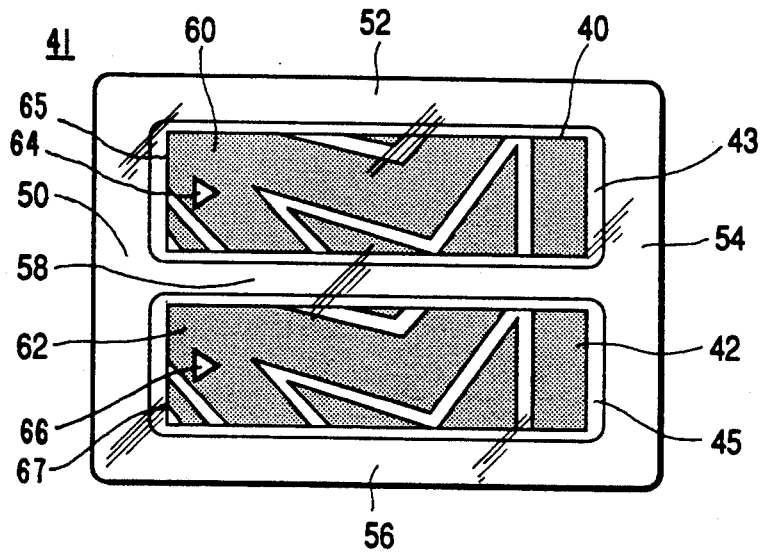
FIG. 3 is a top planar view of an alternate embodiment of the Bowie-Dick test device of FIG. 1.

Referring now to FIG. 3, an alternate embodiment Bowie-Dick test device designated generally 41 is provided wherein two elongated indicator strips of a selectively porous material 40 and 42 are laminated between two layers of clear plastic film in a manner similar to the sheet 12 of FIG. 1. In FIG. 3, the strips 40 and 42 are shown as rectangular, but other shapes could be used such as oval shapes. A region 43 where the laminating layers of clear plastic do not contact one another surrounds strip 40 and a similar region 45 surrounds strip 42. The strips 40 and 42 are oriented in a parallel and spaced apart arrangement, and each is laminated around all four edges. For example, laminated regions even numbers 50 through 56 surround the strips 40 and 42 on the outside while laminated region 58 separates the two strips. The strips 40 and 42 are the same length, are parallel and spaced apart and do not extend beyond one another. Each strip 40 and 42 is imprinted with a pattern of indicator ink 60 and 62, respectively. A metering hole 64, 66 is punched through each strip 40, 42 respectively. In FIG. 3 the holes are each spaced the same distance from the colinear edges 65 and 67 of the strips 40 and 42, respectivley. The metering holes 64 and 66 are closer to edges 65 and 67, respectively, than to the opposite edges. The embodiment shown in FIG. 3 provides a redundant test mechanism wherein both strips should show the same length of darkening for a given vacuum efficiency and steam test cycle. If one of the strips was defectivly delaminated or otherwise was not fully occluded, except at its metering hole, it would more readily darken along its entire length or portion thereof while the remaining strip might show less darkening indicating a flaw in the vacuum efficiency more or less. In one embodiment, the device of FIG. 3 is 2.3281 inches long by 3.250 inches wide and each strip is 2.500 inches long by 0.6875 inches wide, although any size that maintain the same ratio between the laminations, the strips and the hole(s) can be found to perform similarly.

Figure 4:
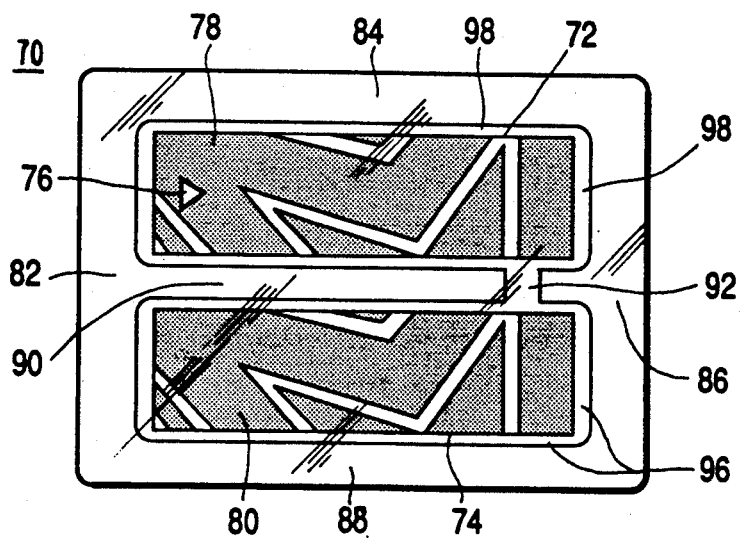
FIG. 4 is a top planar view of a second alternate embodiment of the Bowie-Dick test device of FIG. 1.
Figure 2:
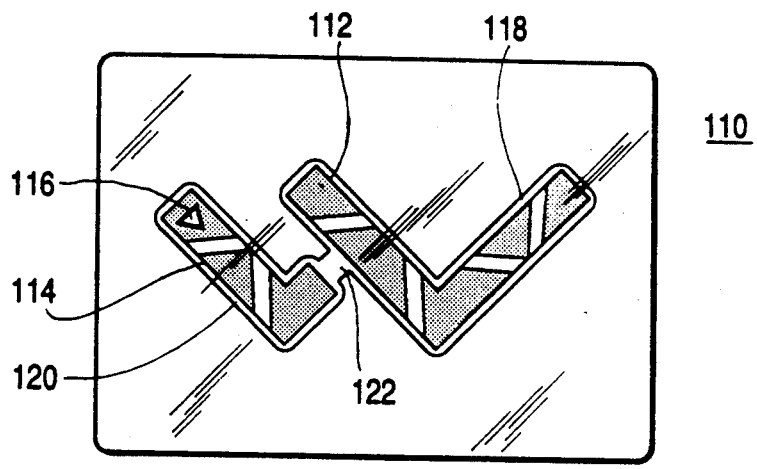
FIG. 2 is a cross-sectional view of the Bowie-Dick test device of the present invention taken along the lines 2—2 in FIG. 1 and showing its laminations.

FIG. 4 shows a device or card 70 which is quite similar to device 41 in FIG. 3 having two parallel and spaced apart strips 72 and 74 of selectively porous layers fully laminated between two clear plastic layers, except for a single hole 76 punched in laminated strip 72. No hole is formed in laminated strip 74. Each strip 72, 74 is imprinted with a pattern of indicator ink 78, 80, respectively. Except for metering hole 76, the strips 72, 74 are totally occluded, top and bottom and around all edges in the regions even numbers 82 through 88 and in region 90 between the strips 72, 74. Unlike FIG. 3, however, the laminated region 90 does not continuously extend between end regions 82 and 86 but is interrupted by the unlaminated bridge 92 which provides a passageway between strip 74 and strip 72 between the clear plastic layers. The passageway is not open to ambient atmosphere except through metering hole 76, but air or fluid present or trapped in strip 74 and in the surrounding unlaminated perimeter 96 around strip 74 is in communication with air, fluid or other gases present or trapped in strip 72 or in the surrounding unlaminated perimeter 98.

Figure 7:
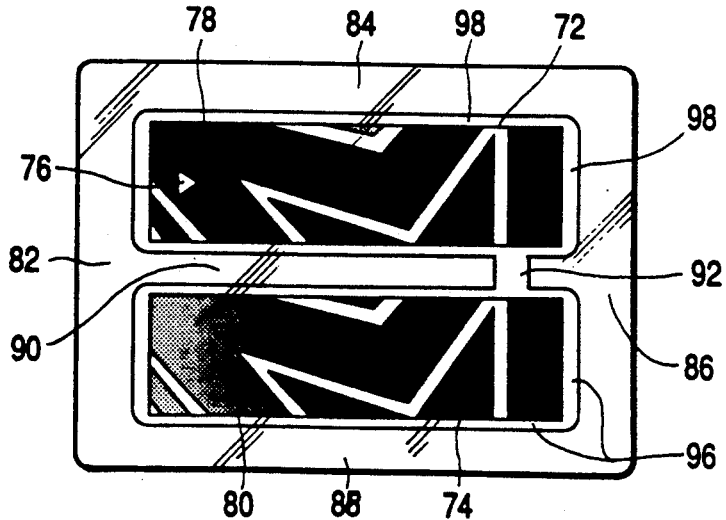
FIG. 7 is a top planar view of the Bowie-Dick test device of FIG. 4 following steam treatment.

The arrangement shown in FIG. 4 provides more challenge to the vacuum. Even if strip 72 becomes fully exposed as indicated in FIG. 7, the rate at which additional strip 74 becomes exposed is governed by the width of bridge 92. With the bridge 92 the effective length of the two strips 72 and 74 as providing a challenge to the vacuum is greater than their real lengths. Note only a portion of strip 74 is exposed and it was exposed through the restricted passage of bridge 92. Hence, the strip configuration shown in FIG. 4 provides great latitude in determining the extent of the meaningful challenge provided by the single device or card 70 while still keeping the device small in shape.

Figure 5:
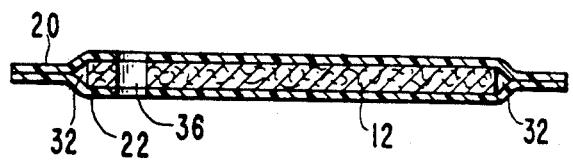
FIG. 5 is a top planar view of a third alternate embodiment of the Bowie-Dick test device of FIG. 1.

While the strips shown in FIGS. 1-4 are rectangular and parallel they could take on other geometrical configurations. For example, FIG. 5 shows a configuartion 110 having a laminated V-shaped strip 112 coupled to a laminated L-shaped strip 114 by bridge 122. The strips are totally occluded by the lamination except for metering hole 116 punched through the L-shaped strip 114. A region 118 surrounds the V-shaped strip 112 where lamination does not occur and this region is connected to region 120 surrounding the L-shaped strip 114 by bridge 122.

Figure 6:
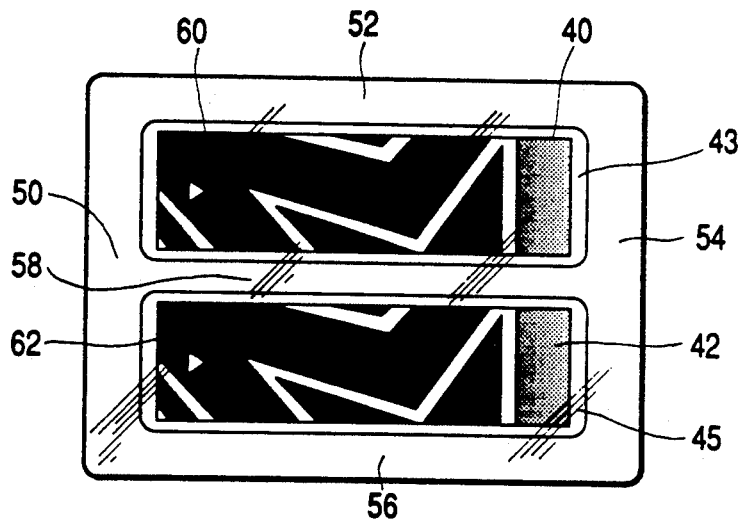
FIG. 6 is a top planar view of the Bowie-Dick test device of FIG. 3 following steam treatment.

In FIGS. 1 and 3 through 5, the steam indicator ink is shown as not having been exposed to a steam sterilization cycle. For comparison, see FIGS. 6 and 7 which are representative of the devices of FIGS. 3 and 4, respectively, having been exposed to a vacuum steam sterilization cycle. Some or most of the ink has turned dark.

What we claim is:

1. A permanent record test device for testing the efficiency with which a steam sterilizer apparatus creates a vacuum satisfying the Bowie-Dick test procedure comprising:
    a sheet comprising a porous material with a steam sensitive indicator ink printed thereon in a predetermined pattern extending from a first point on said sheet to a second point, said sheet serving as a passageway for the passage of steam or air from one of said first point or said second point to the other; and
    a layer of steam and air impermeable material laminated on each side and around the edges of said sheet to substantially totally occlude said sheet from ambient atmosphere, at least one of said layers provided with an aperture to expose said first point to ambient atmosphere.

2. The apparatus of claim 1 wherein said sheet comprises at least two parallel and spaced apart sheets, each lying in the same plane and being totally occluded except for said aperture which comprises an opening which is on the order of ⅛" in diameter when said sheet is on the order of 2.5" in length by 0.6875" in width.

3. The apparatus of claim 2 wherein said aperture is spaced apart from one end of each of said sheets.

4. A permanent record test device for testing the efficiency of a steam sterilizer apparatus to create a vacuum satisfying the Bowie-Dick test procedure comprising:
    at least two parallel and spaced apart planar sheets lying in the same plane, said strips comprising a selectively porous material having a steam sensitive indicator ink printed thereon in a predetermined pattern; and
    a layer of steam and air impermeable material laminated on each side and around the edges of said sheets to form a sandwich structure which totally occludes said sheets from ambient atmosphere except for an aperture created through the laminated material adjacent one of said sheets; and
    a passageway connecting said sheets between said laminated layers, said passageway serving to permit steam to flow between said layers of laminated material from one of said sheets to another.

5. The apparatus of claim 4 wherein each of said sheets is elongated and wherein said aperture is formed through one of said sheets nearer to one end of said sheet than an opposite end thereof and said passageway is formed nearer to the opposite end thereof.

6. A permanent record test device for testing the efficiency of a steam sterilizer apparatus to create a vacuum satisfying the Bowie-Dick test procedure comprising:
    an L-shaped sheet and a V-shaped sheet lying in the same plane, each comprising a selectively porous material with a steam sensitive indicator printed thereon; and
    a layer of steam and air impermeable material laminated on each side and around the edges of said sheets to form a sandwich structure which totally occludes said sheets from ambient atmosphere except for an aperture created through one of said sheets; and
    a passageway connecting said sheets within said laminated layers, said passageway serving to permit steam to flow between said layers of laminated material from one of said sheets to another.

7. The apparatus of claim 6 wherein said passageway is formed adjacent the short side of said L-shaped sheet and said aperture is in the long side of said L-shaped sheet and spaced apart from the edge thereof.

* * * * *

Dedication 5,204,062 — Steven T. Buglino, Apex; Pareshbhai J. Patel, Cary; Bahram B. Rahimzadeh, Durham, all of NC. BOWIE-DICK TEST DEVICE. Patent dated April 20, 1993. Dedication filed February 14, 2000, by the assignee, Steris, Inc.

Hereby dedicates to the public the entire term of said patent.
*(Official Gazette,* April 18, 2000)